US007332640B2

(12) United States Patent
Reyes et al.

(10) Patent No.: US 7,332,640 B2
(45) Date of Patent: Feb. 19, 2008

(54) LIGHT HYDROCARBON SEPARATION USING 8-MEMBER RING ZEOLITES

(75) Inventors: Sebastian C. Reyes, Branchburg, NJ (US); David H. Olson, Pennington, NJ (US); Haiming Liu, Eagleville, PA (US); Karl G. Strohmaier, Port Murray, NJ (US); Jose G. Santiesteban, Baton Route, LA (US)

(73) Assignee: Exxonmobile Research and Engineering Company, Annandale, NJ (US)

( * ) Notice: Subject to any disclaimer, the term of this patent is extended or adjusted under 35 U.S.C. 154(b) by 579 days.

(21) Appl. No.: 10/699,258

(22) Filed: Oct. 31, 2003

(65) Prior Publication Data

US 2005/0096494 A1 May 5, 2005

(51) Int. Cl.
*C07C 7/12* (2006.01)
(52) U.S. Cl. .................. 585/829; 585/821; 585/820; 585/826
(58) Field of Classification Search .............. 585/820
See application file for complete search history.

(56) References Cited

U.S. PATENT DOCUMENTS

| 3,591,488 | A | * | 7/1971 | Eberly et al. | ........... 208/111.15 |
|---|---|---|---|---|---|
| 4,544,538 | A | | 10/1985 | Zones | ................ 423/326 |
| 5,365,011 | A | | 11/1994 | Ramachandran et al. | ... 585/829 |
| 5,418,299 | A | | 5/1995 | Kim et al. | ................ 525/400 |
| 5,466,837 | A | | 11/1995 | Ramachandran et al. | ... 549/533 |
| 6,200,366 | B1 | | 3/2001 | Bulow et al. | ................ 95/101 |
| 6,293,999 | B1 | | 9/2001 | Cheng et al. | ................ 95/96 |
| 6,296,688 | B1 | | 10/2001 | Cheng et al. | ................ 95/101 |
| 6,488,741 | B2 | | 12/2002 | Olson | ................ 95/144 |
| 6,579,347 | B1 | * | 6/2003 | Wakita et al. | ................ 95/135 |

FOREIGN PATENT DOCUMENTS

| EP | 0572239 | A1 | * | 12/1993 |
| EP | 0768111 | | | 4/1997 |
| EP | 0768111 | A1 | | 4/1997 |

| WO | WO02/058820 | A1 | 8/2002 |

OTHER PUBLICATIONS

S. I. Zones, "Conversion of Faujasites to High-silica Chabazite SSZ-13 in the Presence of N, N, N-Trimethyl-1-adamantammonium Iodide," J. Chem. Soc. Faraday Trans., 1991, vol. 87, pp. 3709-3716.
R. T. Yang and E. S. Kikkinides, "New Sorbents for Olefin/paraffin Separations by Adsorption via π-Complexation," AIChE Journal, Mar. 1995, vol. 41, No. 3, pp. 509-517.
J. Padin, Ralph T. Yang, "New sorbents for olefin/paraffin separations by adsorption via π-complexation: synthesis and effects of substrates," Chemical Engineering Science 55 (2000) 2607-2616.
Padin, Joel, and Ralph T. Yang, "New sorbents for olefin/paraffin separations by adsorption via π-complexation: synthesis and effects of substrates," *Chemical Engineering Science* 55 (2000) pp. 2607-2616.
Yang, R.T., and Kikkinides, E.S., "New Sorbents for Olefin/Paraffin Separations by Adsorption via π-Complexation," *AIChE Journal*, vol. 41, No. 3 (Mar. 1995) pp. 509-517.
Zhu, W., Kapteijn, F., and Moulijn, J.A., "Shape Selectivity in the Adsorption of Propane/Propene on the All-Silica DD3R," *Chemical Community* (1999) pp. 2453-2454.
Zones, S.I., "Conversion of Faujasites to High-silica Chabazite SSZ-13 in the Presence of N,N,N-Trimethyl-I-adamantammonium Iodide," *J. Chem. Soc. Faraday Trans.*, 1991, vol. 87, pp. 3709-3716.

* cited by examiner

*Primary Examiner*—Tam M. Nguyen
(74) *Attorney, Agent, or Firm*—Joseph C. Wang; Bruce M. Bordelon

(57) ABSTRACT

The present invention is related to a method for kinetically separating a light hydrocarbon mixture comprising at least two components by preferentially adsorbing a first component on a zeolite adsorbent comprising 8-member rings of tetrahedra as the pore opening controlling hydrocarbon diffusion and alkali metal cations balancing a framework charge, wherein a second component is not preferentially adsorbed. The novel process comprises contacting the light hydrocarbon mixture with a zeolite adsorbent having a $SiO_2/Al_2O_3$ ratio greater than about 50 and less than 200 and further having a diffusion rate at least 50 times greater for the first component as compared to the second component, and then recovering at least one of the first component or the second component.

8 Claims, 7 Drawing Sheets

LIGHT HYDROCARBON SEPARATION USING 8-MEMBER RING ZEOLITES

BACKGROUND OF THE INVENTION

1. Field of the Invention

The present invention relates to a process for the adsorptive separation of low molecular weight hydrocarbons. In particular, the instant invention is directed to a process for separating propylene from propane and mixtures of low molecular weight hydrocarbons.

2. Description of the Related Art

The separation of propylene from low molecular weight hydrocarbon mixtures is an extremely important and large volume operation in the chemical and petrochemical industries. Catalytic cracking and steam cracking are among the most common and large scale processes leading to these mixed hydrocarbon streams. The need to recover propylene from propane-containing streams, in particular, is one of high economic significance in the synthesis of polypropylene elastomers. However, because of the close proximity in boiling points between propylene and propane, these components are presently separated by fractional cryogenic distillation. The large size of the columns and the energy intensity of this distillation process have, however, created large incentives for alternative means of effecting these separations in a more energy-efficient and cost-effective manner.

Some of the leading alternatives to fractional cryogenic distillation involve the use of porous materials that exploit their ability to selectively adsorb some of the components in the mixture. This has given rise to various forms of pressure or temperature swing adsorption (PSA/TSA) processes in which the mixture is first passed through an adsorbent material under conditions where one or more of the components are selectively removed. The loaded material is then typically exposed to a lower pressure and/or higher temperature environment where the adsorbed components are released and recovered at a higher purity level. Economic viability requires adsorbent materials that can deliver high selectivity, high adsorption capacity, and short duration cycles. An additional and critically important requirement is that the material should not catalyze chemical reactions that might lower the recovery of the desired components and/or render the adsorbent inactive.

Among the adsorbents which have been proposed for the recovery of propylene from hydrocarbon mixtures are ion exchange resins, mesoporous solids, activated carbons, and zeolites. Ion exchange resins and mesoporous solids usually exploit equilibrium adsorption properties in which one of the components is selectively adsorbed over suitably dispersed chemical agents. They principally rely on the adsorption affinity of cationic active centers, such as Ag and Cu, for the double bond in propylene ($\pi$-complexation). The characteristic time associated with the adsorption cycle is that required to bring the mixture close to thermodynamic equilibrium with the adsorbent. Because of the strong propylene-metal ion interaction, these systems generally require heat input to achieve rapid and complete propylene desorption. The relative rates of diffusion of the various components within the adsorbent are of secondary importance.

A second class of processes relies on the relative rates of diffusion within the adsorbent to carry out the separation. Two related cases are of interest here. In one extreme case, the separation is achieved by excluding the diffusion of some of the components into the adsorbent. This situation, in principle, leads to a maximum separation efficiency. The second case exploits a sufficiently large difference in diffusion rates that allow the preferential uptake of some of the components within a predetermined adsorption time. This case is commonly referred to as a kinetic-based separation scheme and is the method of choice to be used in conjunction with the materials disclosed in the present invention.

Activated carbons and zeolites typically resort to a combination of adsorption affinity and diffusion control. Carbons are usually activated to very high surface area forms in order to provide textural properties that simultaneously target the optimization of adsorption affinity and diffusion control. Using similar principles, zeolites have become even more attractive than activated carbons because of the ever-increasing possibilities afforded by new material synthesis procedures. Zeolites allow for a more flexible and precise control of critical properties such as chemical composition, internal surface area, pore volume, and window sizes. Chemical composition, internal surface area and pore volume are key variables controlling the adsorption capacity of the material. The tetrahedrally coordinated atoms, on the other hand, give rise to connecting windows of precise dimensions that control diffusional transport in and out of the crystallites.

Eight-membered ring zeolites, in particular, have been actively investigated for the separation of low molecular weight hydrocarbons because the window sizes of these zeolites are comparable to the molecular dimensions of low molecular weight molecules and because many afford high adsorption capacities. A typical example is the Linde type A zeolite that is characterized by a set of three-dimensional interconnected channels having 8-membered ring window apertures. The effective size of the windows depends on the type of charge-balancing cations. This has given rise to the potassium (3A), sodium (4A), and calcium (5A) forms, which have nominal window sizes of about 3 Å, 3.8 Å, and 4.3 Å, respectively. Thus, for example, EP-B-572239 discloses a PSA process for separating an alkene, such as propylene, from a mixture comprising said alkene and one or more alkanes by passing the mixture through at least one bed of zeolite 4A at a temperature above 323 K to preferentially adsorb said alkene and then desorbing the alkene from the bed. EP-A-943595 describes a similar process in which the zeolite adsorbent is zeolite A having, as its exchangeable cations, about 50% to about 85% sodium ions, about 15% to about 40% potassium ions and 0% to 10% of other ions selected from Group IA ions (other than sodium and potassium), Group IB ions, Group IIA ions, Group IIIA ions, Group IIIB ions and lanthanide ions.

In zeolites, it is well-accepted that the control of window size is important for achieving high separation selectivities. For a given zeolite structure type, the effective size of the windows can be sometimes further tuned by partially blocking or unblocking the windows with suitable charge-balancing cations.

In addition to window size control, an important requirement is that the adsorbent material should not catalyze any chemical reactions. This is particularly important for separating mixtures containing olefins, which can readily oligomerize on mildly acidic sites even at relatively low temperatures. Any residual catalytic activity of the adsorbent leading to detrimental reactions has to be avoided. These reactions not only lower the recovery of the desired components, but they are also likely to render the adsorbent inactive. The double bonds in the olefins, for example, are particularly prone to attack, even by mildly acidic centers and this may severely limit the temperature and partial pressures at which the separation process can be carried out.

In an effort to control chemical reactivity more reliably, there is a growing interest in the use of non-acidic, all-silica zeolites. Since these siliceous zeolites require no extra-framework balancing cations, the size of the windows is uniform and determined solely by the crystal structure. Thus, for example, the potential of deca-dodecasil 3R (DD3R) for separating propane and propylene has been very recently reported. See Zhu, W., Kapteijn, F., and Moulijn, J. A., "Shape Selectivity in the Adsorption of Propane/Propene on the All-Silica DD3R," Chem. Commun. 2453-54 (1999). This crystalline microporous silicate has a two-dimensional pore system formed by 8-membered rings of tetrahedrally coordinated atoms with a nominal window size of 3.6 Å×4.4 Å (see Atlas of Zeolites Framework Types, Fifth Revised Edition, pages 108-109, 2001). Reported adsorption measurements on this material indicate that whereas propylene is able to diffuse to the interior of the crystallites, propane is largely excluded. However, the size of the DD3R windows appears to be so close to the effective kinetic diameter of propylene that the diffusion rates are very low, and this could lead to undesirably long adsorption and desorption cycles. Cycle duration can, in principle, be reduced by appropriate reductions in crystal size, but such changes are not always possible with the known synthetic procedures. Furthermore, the low dimensionality (2-D) and the high framework density (17.6 T/1000 Å$^3$) suggest that DD3R has only a limited capacity for adsorbing propylene.

Relying on similar arguments of non-acidity, U.S. Pat. Nos. 6,293,999 and 6,296,688 disclose the use of AlPO-14 (AFN) for separating propylene from propane. Although AlPO-14 possesses a set of three-dimensional interconnecting 8-ring windows, only one of them is large enough to allow the passage of propylene; therefore, AlPO-14 effectively has a 1-dimensional diffusion system for hydrocarbons and it exhibits relatively low adsorption capacity. Moreover, with a nominal window size dimension of only 3.3 Å×4.0 Å (Atlas of Zeolites Framework Types, Fifth Revised Edition, pages 36, 37, 2001), the diffusion of propylene should be slow and associated with undesirably long adsorption cycles. Further, the above two patents reveal that AlPO-14 exhibits adsorption hysteresis, behavior that indicates that not all of the propylene is desorbed at low temperatures. This feature becomes dominant at lower temperatures; at 25° C. it reduces the effective reversible adsorption by ~60% and thus decreases the effectiveness of this adsorbent.

U.S. Pat. No. 6,488,741 B2 teaches the use of two pure silica zeolites and one very high silica zeolite for the kinetic separation of propylene from propylene/propane mixtures. While the two pure silica zeolites, Si—CHA and ITQ-3, have desirable properties—i.e., high ratios of diffusion rate parameters and satisfactory adsorption capacities—they are very difficult and expensive to synthesize, thereby bringing their practicality into question.

BRIEF SUMMARY OF THE INVENTION

In accordance with the present invention, the potassium form of dealuminated SSZ-13 has been found to be very effective for the kinetic-based separation of propylene and propane through a unique combination of diffusion rate constants, capacity, and chemical inertness. Unlike the situation with DD3R or AlPO-14, with the present material the diffusion rate constant for propylene is not only much higher than for propane, it is at the same time also high enough to allow short adsorption/desorption cycles that are economically viable.

In particular, the instant invention is related to a method for kinetically separating a light hydrocarbon mixture comprising at least two components by preferentially adsorbing a first component on a zeolite adsorbent comprising 8-member rings of tetrahedra as the pore opening controlling hydrocarbon diffusion and alkali metal cations balancing a framework charge, wherein a second component is not preferentially adsorbed. The novel process comprises contacting the light hydrocarbon mixture with a zeolite adsorbent having a $SiO_2/Al_2O_3$ ratio greater than about 50 and less than 200 and further having a diffusion rate at least 50 times greater for the first component as compared to the second component, and then recovering at least one of the first component or the second component. The preferred zeolite adsorbent SSZ-13, which is an isotype of chabazite.

The invention further comprises dealuminating the zeolite adsorbent before the contacting step. It is preferred that the dealuminating step comprises steaming the zeolite adsorbent.

DETAILED DESCRIPTION OF THE INVENTION

Figure 1:
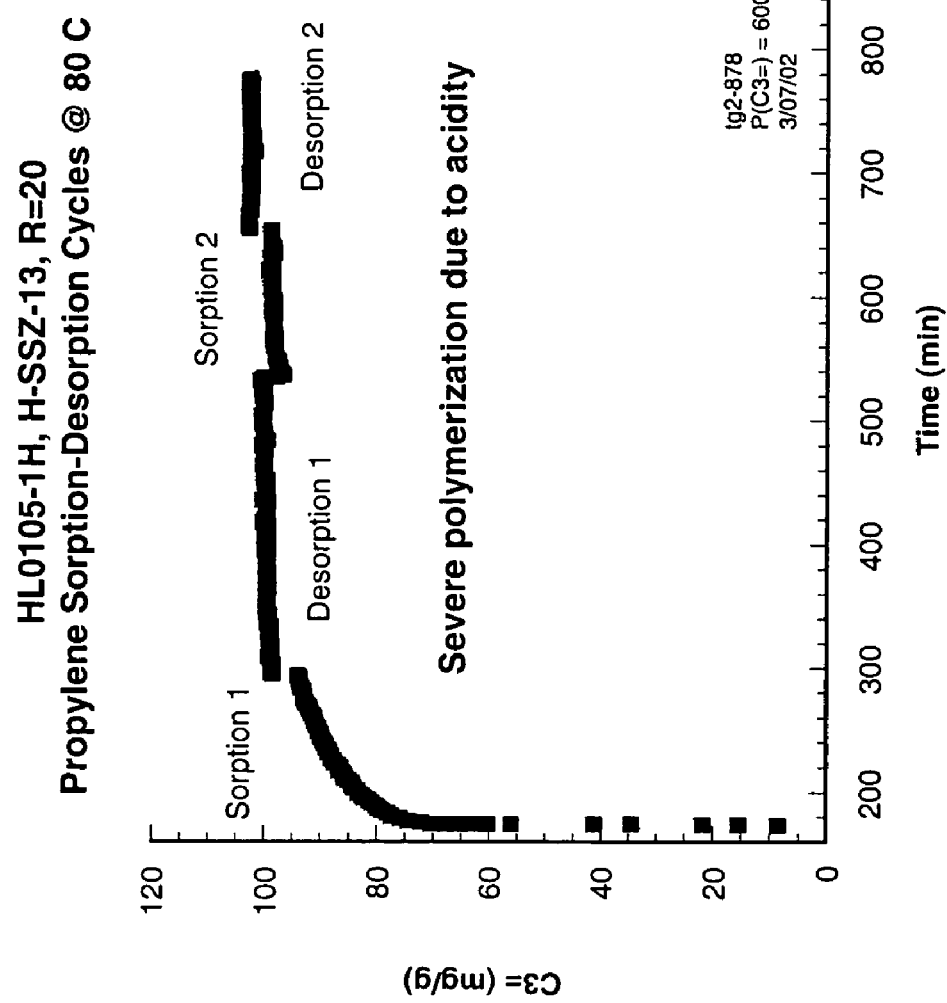
FIG. 1 illustrates the detrimental effects of acidity on successive adsorption/desorption cycles of propylene over H-SSZ-13 ($SiO_2/Al_2O_3$=20) at 353 K and 80 kPa.

Zeolites are commonly classified as large-pore, medium-pore or small-pore and, in most cases, the channel systems of such zeolites are accessed via 12-membered rings (or larger), 10-membered rings or 8-membered rings (or smaller), respectively.

The zeolites of this invention have 8-membered rings of tetrahedra as diffusion controlling ring size, thereby excluding access to the pore system by larger hydrocarbons. A large number of zeolites have 8-membered rings of tetrahedra as the largest ring size. These zeolites are referred to as 8-membered ring or small-pore zeolites.

The Structure Commission of the International Zeolite Association has assigned three letter structure type codes to all zeolites of known structure. Frequently, the different names have been assigned to materials having the same structure type, such materials being referred to as isotypes. This may occur in cases where the materials have a composition different from the material that was the basis for the original assignment of the structure type code. A list and description of these 8-membered ring structures is found in U.S. Pat. No. 6,488,741 B2 to Olson and in the *Atlas of Zeolite Structure Types* by W. M. Meier, D. H. Olson and Ch. Baerlocher, Elsevier, 1996, the disclosures of which are both incorporated by reference herein.

Of particular interest in the present invention is the structure type code CHA, which is derived from the zeolite mineral chabazite. SSZ-13, an isotype of the CHA structure type, is of particular interest in the present invention. The CHA structure type was chosen because it has relatively high adsorption capacity for propylene, ~120 mg/g, and has a three-dimensional channel system. The CHA isotype SSZ-13 is of interest because it is much more readily synthesized than the pure silica CHA isotype, referred to as Si—CHA. (See S. I. Zones, "Conversion of Faujasite to High-silica Chabazite SSZ-13 in the Presence of N.N.N-Trimethyl-1-adamantammonium Iodide," J. Chem. Soc. Faraday Trans., 1991, 87, 3709; U.S. Pat. No. 4,544,538 to Zones).

Other preferred adsorbents are zeolites having 8-member rings that have a relatively high $SiO_2:Al_2O_3$ ratio and are substantially acid free. Relatively high $SiO_2:Al_2O_3$ ratio is defined as a ratio of at least about 50 and less than about 200, more preferably at least about 80 and less than about 180. For efficient, long-term operation of the adsorption process, it is critical that the adsorbent have either essentially no acidity or sufficiently low acid activity such that polymerization of olefins does not occur. Acidic sites in the adsorbent will result in polymerization of the desired olefins that would require thermal activation to remove. Accordingly, the term "substantially acid-free" is used herein to encompass zeolites that do not polymerize olefins in a manner that would prevent long-term operation of the adsorption process. In addition to the cost of the thermal treatment, there is a substantial time requirement as well, both of which would significantly reduce operating efficiency. Equilibrium should be reached in under 60 minutes, more preferably under 30 minutes, and even more preferably in less than 2 minutes.

Control of acidity can be done in several ways. One method of reducing acidity is to subject the zeolite to ion exchange with low activity metal cations. It is known in the art that the preferred cations for this purpose are alkali metal cations, such as sodium, potassium or cesium. The larger cations have the advantage of weaker interactions with olefins and, hence, lower temperature and/or faster desorption of the desired olefin. U.S. Pat. No. 6,488,741 to Olson discloses that the preferred method in the art of avoiding acidity and ensuring the desired $SiO_2:Al_2O_3$ ratio is to synthesize the zeolite adsorbent with the lowest possible aluminum content. The instant invention discloses a novel method of reducing acidity that is more advantageous and less costly than synthesizing the zeolite with a lower aluminum content.

In the present case, acidity is reduced by performing a dealuminating step to reduce the aluminum content of the zeolite adsorbent. The preferred method of dealuminating is to steam the adsorbent, preferably at a temperature between 923 K and 1123 K, more preferably between 973 K and 1073 K and most preferably between 973 K and 1023 K, and at a water pressure between 50 kPa and 202 kPa, for a time period between 1 minute and 20 hours.

The discovery that substantially acid-free zeolites having 8-member rings and $SiO_2:Al_2O_3$ ratios of between about 50 and 200 make good adsorbents for separation of propylene from hydrocarbon mixtures is of considerable practical importance. While pure silica zeolites of the CHA and ITE structure types are operable, specific zeolites of this type may currently be very expensive to prepare in small quantities, let alone the large amounts of zeolite that would be required for industrial application. The ability to select well-known and relatively inexpensive 8-membered zeolites which can then be made suitable for use by routine treatment steps is an essential prerequisite for the commercial application of an industrial process for separation of propylene by zeolite adsorbents.

The zeolites of the present invention are characterized by their unexpectedly high diffusional distinction between propylene and propane. This distinction can be quantified in terms of the ratio of the diffusional coefficients for these two hydrocarbons, i.e., the ratio of $D_{propylene}/D_{propane}$. The effectiveness of an adsorbent for separation increases with the magnitude of this ratio, which is referred to herein as $R_D$. It is well accepted in the art that an adsorbent having an $R_D$ greater than about 25, and preferably greater than 50, would be an effective separation adsorbent for a two-component system.

Where the $R_D$ value for propylene/propane approaches unity, there is no kinetic-based preferential adsorption of one component over the other. As the value of $R_D$ becomes less or greater than unity, there is a preferential selectivity by the adsorbent for one of the two components. When comparing an $R_D$ value of propylene relative to propane, a ratio larger than unity indicates that propylene is adsorbed more rapidly than propane within the adsorbent, while an $R_D$ value less than unity would indicate that propane is adsorbed more rapidly by the adsorbent.

The zeolites of the instant invention have a $R_D$ ratio (propylene/propane diffusion ratio) of greater than fifty (50), preferably greater than one hundred (100), more preferably greater than two hundred (200), and most preferably greater than five hundred (500).

Another important adsorbent property of a zeolite is its adsorption capacity, for example as measured by the weight of hydrocarbon adsorbed per unit weight of adsorbent. A zeolite's capacity to adsorb propylene is commonly defined as the number of milligrams of propylene adsorbed per gram of zeolite at equilibrium. Equilibrium condition is defined as the lack of additional change in the amount of propylene adsorbed by the zeolite. In principle, the higher the adsorption capacity, the less the adsorbent that will be required to separate a given quantity of hydrocarbon, e.g., propylene, for an adsorbent having a given $R_D$. The zeolites of this invention are also characterized by their high adsorption capacity. Specifically, the zeolite of the present invention has a propylene adsorption capacity of greater than 40 milligrams (mg) propylene per gram (g) zeolite measured at 353 K and a propylene pressure of 80 kPa. The zeolite's propylene adsorption capacity at that temperature and pressure is preferably at least 60 mg/g and more preferably 100 mg/g.

A high $R_D$ value is required to achieve effective kinetic separation, and a moderate to high adsorption capacity is required to make the separation process practical.

In the description that follows, unless otherwise stated, adsorption capacities will be the values determined when the feed is at 80 kPa pressure and the adsorption chamber is at 353° K. Several different modes of making these measurements are feasible.

Another method of controlling a zeolite's behavior as an adsorbent for use in practicing this invention is by controlling the size of the zeolite crystal. Adjusting this size, typically achieved during the zeolite synthesis step, will allow the attainment of practical cycle times, as in a pressure swing adsorption process (PSA process). The adsorption rate varies as the inverse square of the radius of the crystal. Thus a change in the average crystal size by a factor of 10 will produce a factor of 100 difference in the adsorption and desorption step times. Accordingly, careful attention must be given to the control of the size of the zeolite crystals employed. It is preferable that the size of the zeolite crystal is no larger than 1.0 microns and more preferably no larger than about 0.1 to 0.4 microns.

The novel separation process of the instant invention involves contacting a mixture containing propylene and one or more hydrocarbons—in particular, propane—that exists either as a gas, liquid or mixed phase with at least one of the class of zeolites described above for a period of time to selectively adsorb propylene within the internal pore structure of the zeolite. The components of the hydrocarbon mixtures that are not adsorbed are thus carried off. The propylene is thereafter recovered from the internal pore structure of the zeolite by conventional desorbing techniques, such as stripping with another gas, pressure change, temperature change or a combination of these methods. A single or multistage pressure swing adsorption process (PSA process) is typical of the type of configuration in which this invention may be practiced. Similarly, a single or multistage membrane-based process may be employed. The processes of this invention can also be conducted in flow type (continuous) systems, e.g., a continuous chromatographic type operation. In such a flow type system, a hydrocarbon mixture is passed through a bed containing at least one of the class of zeolites described above. Because of the high selectivity of the zeolites used in practicing this invention, the desired propylene is adsorbed or retained in the bed, while the remaining hydrocarbons are removed. By this process, a highly purified propylene product can be obtained.

The exact temperature at which the novel processes of this invention are conducted will depend upon the type of separation method employed. The temperature, however, must be maintained below that at which a chemical reaction might occur, e.g., below the oligomerization or cracking temperature. The temperature should thus be maintained below about 523 K. Preferably, the processes of this invention can be conducted in the temperature range between 173 K and about 423 K, and more preferably between 253 K and 423 K.

In the above, materials are described that are useful for the separation of propylene from propane. In this embodiment, propylene is the gas phase component preferentially adsorbed. In the subsequent desorption step, separation and recovery of high purity propylene is achieved. It should be understood that for a different pair of light hydrocarbons, the gas phase component not preferentially adsorbed may be the desired hydrocarbon. In this instance, the non-adsorbed or slowly adsorbed hydrocarbon is separated in high purity and subsequently the adsorbed component is desorbed before this process is repeated.

Thus, the detailed discussion concerning propylene/propane separation illustrates the potential of 8-membered ring zeolites for kinetic based separation. These teachings may in turn be applied to other light hydrocarbon pairs, or mixtures, and cases where either the fast adsorbing or the slow adsorbing component is the desired higher value product.

The process of the invention can be carried out in a system comprising a single adsorption bed or a plurality of adsorption beds operated either in phase or out of phase. With a system comprising a single adsorption bed or a plurality of beds operated in phase, the adsorption step must be periodically stopped to permit desorption of the adsorbate from the bed(s). Conversely, when a plurality of adsorption beds are employed in parallel and operated out of phase, one or more beds can be in adsorption service adsorbing the desired gas component, while one or more other units are undergoing regeneration to desorb and collect the adsorbed gas component. Operation of the adsorption process of the invention is cyclical. In the preferred adsorption process, cycles are repeatedly carried out in a manner such that production of the desired product gas is substantially continuous. In the preferred embodiment, therefore, the process is carried out in a system comprising a plurality of adsorption beds arranged in parallel and operated out of phase, such that at least one bed is always in the adsorption phase while another is always in the adsorbent regeneration phase.

The process of the invention may be operated as either a pressure swing adsorption (PSA) process or a temperature swing adsorption (TSA) process. In either case, the precise steps used in carrying out the separation are not critical to the invention.

In general, the basic steps in a PSA process may include an adsorption vessel pressurization step, an adsorption step and an adsorbent desorption step. During the vessel pressurization step, the pressure in the adsorption vessel in which the adsorption process is carried out is raised to the desired adsorption pressure. During the adsorption step, a gaseous propylene- and propane-containing feed is passed through the adsorption vessel at the desired adsorption pressure. As the feed gas passes through the adsorption vessel, a propylene-enriched component is adsorbed and a propylene-depleted non-adsorbed gas fraction passes out of the adsorption vessel. The bed desorption step is carried out by reducing the pressure in the adsorption vessel so as to desorb the propylene-enriched product gas from the vessel.

The temperature at which the adsorption step of the PSA process is carried out is not critical but in general will be between about 173 K and about 523 K, or more preferably between about 253 and about 473 K. The upper temperature is selected so as to achieve a significant loading onto the material and to avoid the possibility of any unwanted reactions, such as oligomerization and/or polymerization of the propylene. The pressures at which the adsorption and adsorbent desorption steps are carried out are likewise a matter of choice, and in general, these steps can be carried out at any of the usual pressures employed for gas PSA processes. The pressure at which the adsorption step is carried out is determined by economics. Typically, the adsorption step is carried out at propylene partial pressures in the range of about 3 kPa to about 300 kPa, and preferably in the range of about 5 kPa to about 200 kPa. Typically, the adsorbent desorption step is carried out at pressures in the range of about 0.1 kPa to about 10 kPa, and preferably in the range of about 0.2 kPa to about 5 kPa.

Where the process of invention is operated as a TSA process, the adsorption step is carried out at a first temperature and an adsorbent desorption step is carried out at a second higher temperature so as to desorb the propylene-enriched component adsorbed during the production step. In this case, the adsorption step is carried out at temperatures in the range of about 173 K to about 523 K, preferably in the range of about 253 K to about 423 K, while the adsorbent desorption step is carried out at temperatures in the range of about 323 K to about 523 K, preferably in the range of about 323 K to about 473 K. The adsorption and desorption steps in a TSA process are typically carried out at propylene partial pressures in the range of about 10 kPa to about 500 kPa, and preferably in the range of about 20 kPa to about 300 kPa.

The invention will now be more particularly described with reference to the following Examples and the accompanying drawings, which are presented for illustration purposes only and are not to be taken as limiting the present invention in any way.

EXAMPLES

Example 1

Synthesis of SSZ-13

SSZ-13 was synthesized following the method of Zones [S. I. Zones, J. Chem. Soc. Faraday Trans., 1991, 87 (22), 3709]. The hydrothermal reaction was carried out at 408 K and at a stirring rate of 120 rpm for 2 days in a 300 ml Parr stainless steel mini-reactor equipped with a stirrer drive system. The reactants mixture was composed of 2.0 g $NH_4$—Y ($SiO_2/Al_2O_3$=5.2), 3.2 g template (N,N, N-trimethyl-1-adamantammonium iodide, 10 mmol), 20.0 g PQ 'N'™ brand sodium silicate (37.2 wt. %, $SiO_2/Na_2O$=3.22), 16 ml 1.0 M NaOH, and 32.0 ml $H_2O$. The preparation yielded about 4.8 g as-synthesized SSZ-13.

Example 2

Preparation of H-SSZ-13

The as-synthesized SSZ-13 of Example 1 was calcined in a tube furnace at 813 K in $N_2$ for 2 hours and then at 813K in air for 2 hours. The calcined SSZ-13 was then ammonium exchanged with 1.0 M $NH_4Cl$ to yield $NH_4$-SSZ-13. A temperature programmed ammonia desorption measurement on $NH_4$-SSZ-13 indicated $SiO_2/Al_2O_3$=20. $NH_4$-SSZ-13 was calcined in a muffle furnace at 773 K for 2 hours to produce H-SSZ-13 ($SiO_2/Al_2O_3$=20).

Example 3

Preparation of K-SSZ-13

A sample of K-SSZ-13 ($SiO_2/Al_2O_3$=20) was prepared by exchanging a portion of the H-SSZ-13 (20) of Example 2 with 1.0 N KCl, during which the pH of the slurry was adjusted to 8.3 using 0.1 N KOH solution.

Example 4

Preparation of Dealuminated SSZ-13

A dealuminated SSZ-13 ($SiO_2/Al_2O_3$=160) sample was prepared as follows. A portion of the as-synthesized SSZ-13 of Example 1 was program heated in flowing nitrogen, then air, at 1073 K. This material was then converted to ammonium form by ion exchanging it with 1.0 M $NH_4Cl$. The product was then steamed 15 hours at 973 K and a $H_2O$ partial pressure of between 50 and 100 kPa. This steamed material was then ammonium exchanged with 1.0 M $NH_4Cl$.

A temperature programmed ammonia desorption measurement indicated that $SiO_2/Al_2O_3$ of the crystalline component is 160 (assuming all ammonia is from the crystalline component and using a crystallinity value estimated from its adsorption capacity).

Example 5

Preparation of K-SSZ-13

A sample of K-SSZ-13 ($SiO_2/Al_2O_3$=160) was prepared by heating, in air, the sample of Example 4 for 60 minutes at 813 K and then exchanging the product with 0.5 N KCl, during which the pH of the slurry was adjusted to 8.4 using KOH solution.

Example 6

Adsorption of Propylene Over H-SSZ-13

In a thermogravimetric analyzer, propylene (80 kPa) was passed over the H-SSZ-13 ($SiO_2/Al_2O_3$=20) of Example 2 at 353 K for 120 minutes. The weight gain was 100 mg/g. The gas flow was then switched to 100% nitrogen gas and continued for 240 minutes. The weight gain remained at 100 mg/g, indicating that over this acidic zeolite, propylene polymerization occurred, which produced high molecular weight hydrocarbons that do not desorb or decompose at 353 K. See FIG. 1.

Example 6, which uses H-SSZ-13 ($SiO_2/Al_2O_3$=20) as the adsorbent, demonstrates that an acidic zeolite such as this cannot be used as adsorbent for propylene separation since polymerization will occur, producing high molecular weight hydrocarbons, thereby reducing the effectiveness of the adsorbent, consuming propylene and requiring elevated temperatures for regeneration.

Example 7

Adsorption of Propylene Over K-SSZ-13

Figure 2:
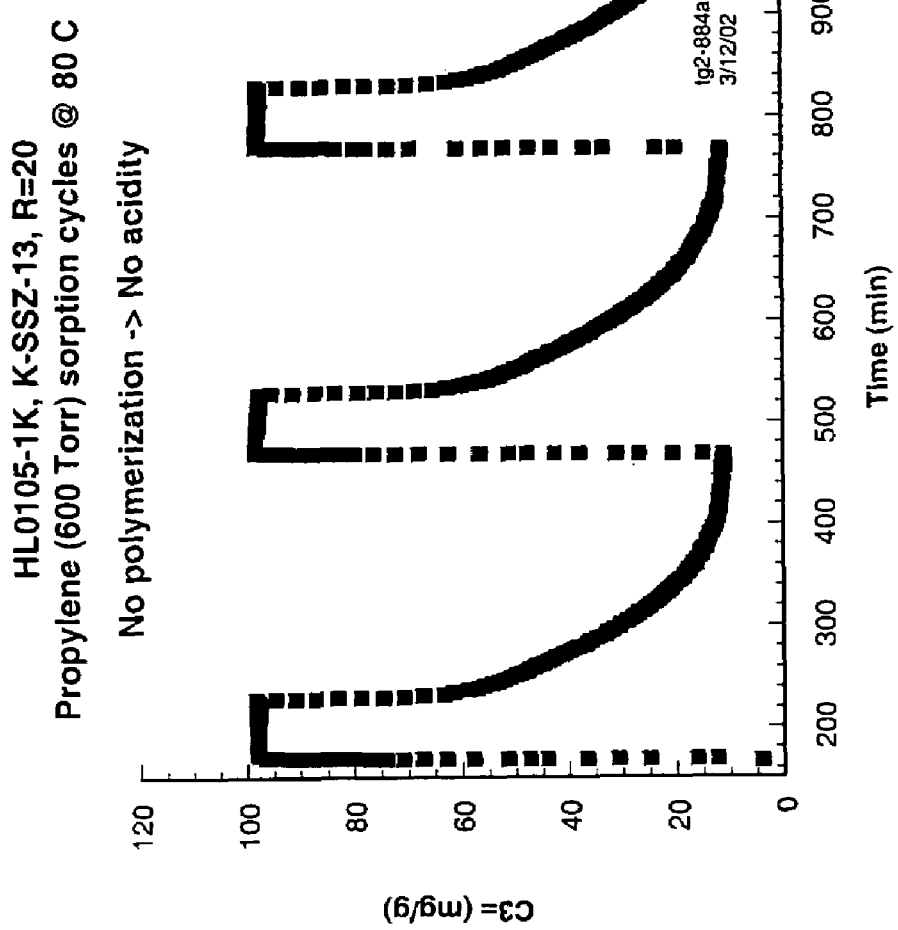
FIG. 2 illustrates adsorption/desorption cycles of propylene over alkali metal exchanged K-SSZ-13 ($SiO_2/Al_2O_3$=20) at 353 K and 80 kPa. It demonstrates the relatively slow desorption of propylene due to strong interaction with the potassium cations in the zeolites.
Figure 4:
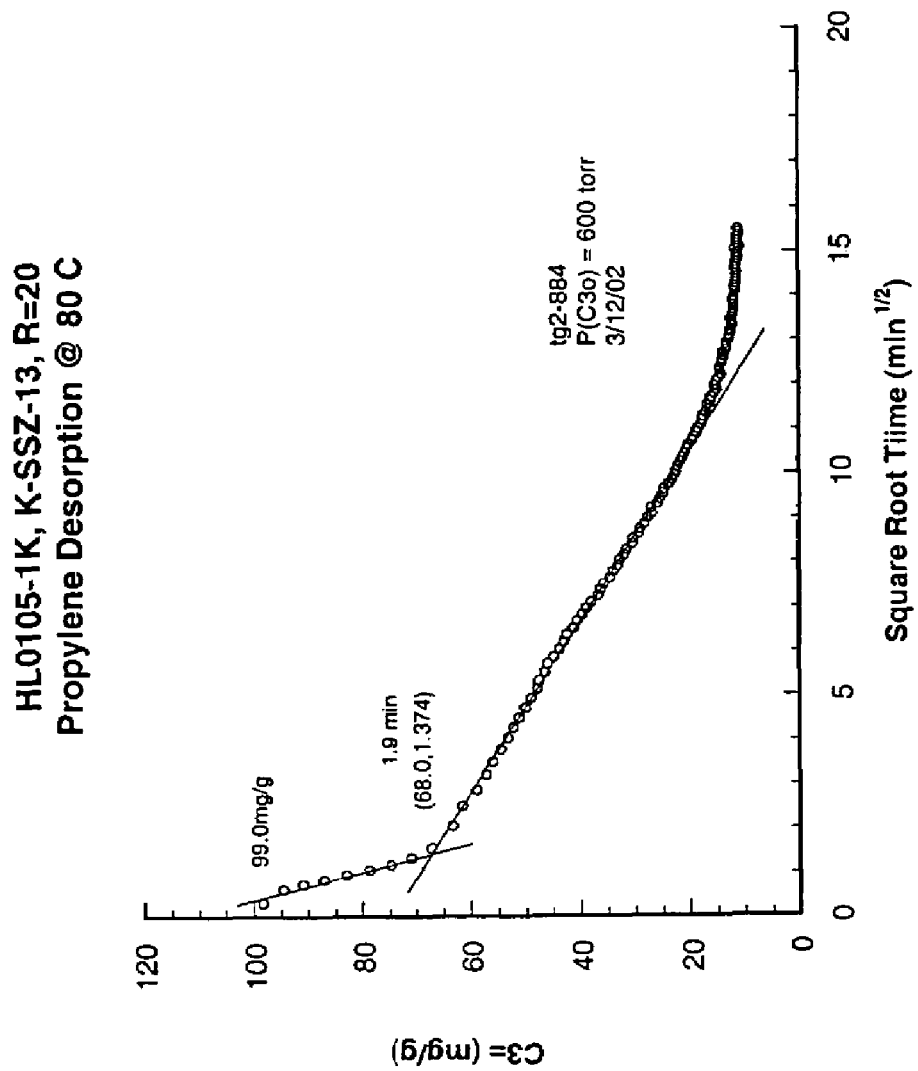
FIG. 4 shows the rate of propylene desorption from K-SSZ-13 ($SiO_2/Al_2O_3$=20) at 353 K and 80 kPa. This figure illustrates the slow desorption of propylene referred to in FIG. 2.

In a thermogravimetric analyzer, propylene (80 kPa) was passed over the K-SSZ-13 ($SiO_2/Al_2O_3$=20) of Example 3 at 353 K for 60 minutes. The weight gain reached a constant value of 99 mg/g within ~5 minutes. The gas flow was then switched to 100% nitrogen gas and continued for 240 minutes (see FIG. 2). Desorption occurs in two steps: The first step is a very rapid weight loss step followed by a much slower rate of desorption (see FIG. 4). The very rapid weight loss, occurring during the first 2 minutes and over the weight range of 99 mg/g down to 68 mg/g, corresponds to desorption of ~31% of the propylene. The onset of the slow sorption corresponds to a sorption level of ~1.1 $C_3^=/K^+$, consistent with strong interaction of the one propylene molecule with each potassium ion.

Example 8

Adsorption of Propylene Over K-SSZ-13 Three Times

In a thermogravimetric analyzer using the K-SSZ-13 ($SiO_2/Al_2O_3$=20) of Example 3, the experiment of Example 7 was repeated 3 times. For each of the three cycles the amount of propylene adsorbed or desorbed was essentially identical for a given elapsed cycle time indicating that there is no propylene polymerization at these conditions over this adsorbent (see FIG. 2).

Examples 7 and 8, which use K-SSZ-13 ($SiO_2/Al_2O_3=20$) as the adsorbent, show that converting the H-form of the zeolite to the potassium form dramatically reduces, and may even eliminate, the polymerization reaction. Thus, alkali metal exchange is an effective means of eliminating the propylene polymerization problem.

Example 9

Adsorption of Propylene Over K-SSZ-13

Figure 3:
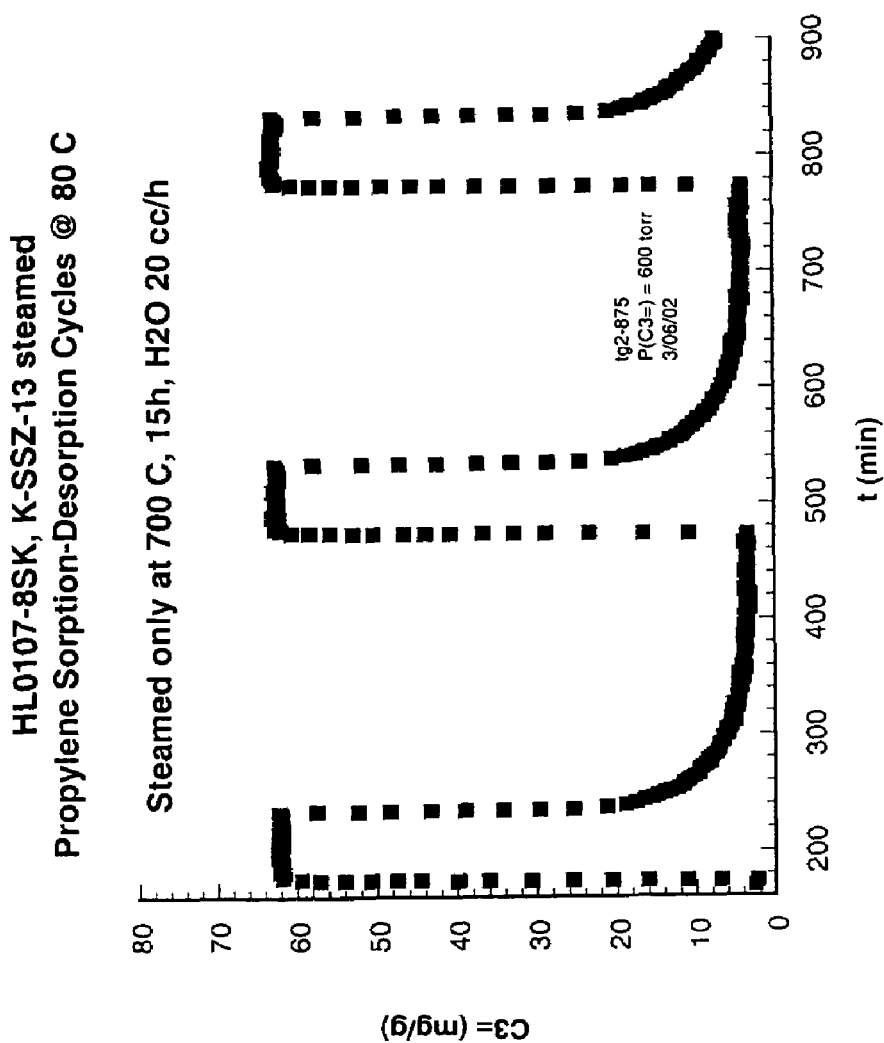
FIG. 3 illustrates the beneficial effects the higher silica-to-alumina ratio produced by the steaming and the more rapid desorption of propylene, compared with that shown in FIG. 2, due to the concomitant lower alkali metal cation concentration, on the adsorption/desorption cycles of propylene over dealuminated K-SSZ-13 ($SiO_2/Al_2O_3$=160) at 353 K and 80 kPa.
Figure 5:
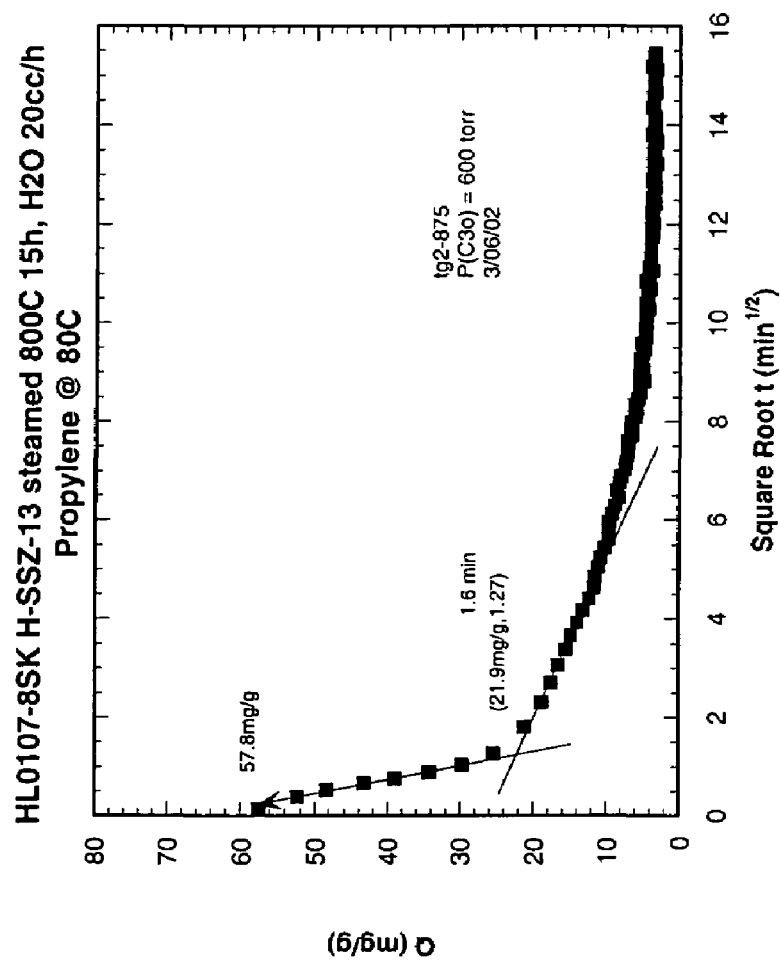
FIG. 5 shows the rate of propylene desorption from dealuminated K-SSZ-13 ($SiO_2/Al_2O_3$=160) at 353 K and 80 kPa. This figure illustrates the fast desorption of propylene referred to in FIG. 3.

In a thermogravimetric analyzer, propylene (80 kPa) was passed over the K-SSZ-13 ($SiO_2/Al_2O_3=160$) of Example 5 at 353 K for 60 minutes. The weight gain reached a constant value of 58 mg/g within ~5 minutes. The gas flow was then switched to 100% nitrogen gas and continued for 240 minutes (see FIG. 3). Desorption occurred in two steps: a very rapid weight loss step followed by a much slower rate of desorption (see FIG. 5). The very rapid weight loss occurred during the first 2 minutes and over the weight range of 58 mg/g down to 22 mg/g, corresponding to desorption of ~62% of the propylene. The onset of the slow sorption corresponds to a sorption level of ~4.4 $C_3^=/K^+$.

Examples 7 and 9 show that dealumination of the zeolite is important in producing an effective adsorbent. An effective adsorbent must exhibit a relatively rapid adsorption and desorption of propylene. We see that the dealuminated K-SSZ-13 ($SiO_2/Al_2O_3=160$) in Example 9 desorbs 62% of its sorbed propylene very rapidly compared with only 31% for K-SSZ-13 ($SiO_2/Al_2O_3=20$) in Example 7, which was not dealuminated.

Example 10

Adsorption of Propylene Over K-SSZ-13 Three Times

In a thermogravimetric analyzer using the K-SSZ-13 ($SiO_2/Al_2O_3=160$) of Example 5, the experiment of Example 9 was repeated 3 times. For each of the three cycles, the amount of propylene adsorbed or desorbed was essentially identical for a given elapsed sorption time indicating that there is no propylene polymerization at these conditions over this adsorbent (see FIG. 3).

Examples 9 and 10 also show that converting the H-form of the dealuminated zeolite to the potassium form eliminates the polymerization reaction. Thus, again, alkali metal exchange is an effective means of eliminating the propylene polymerization problem.

Example 11

Diffusion Ratio of Propylene Compared to Propane

Figure 6:
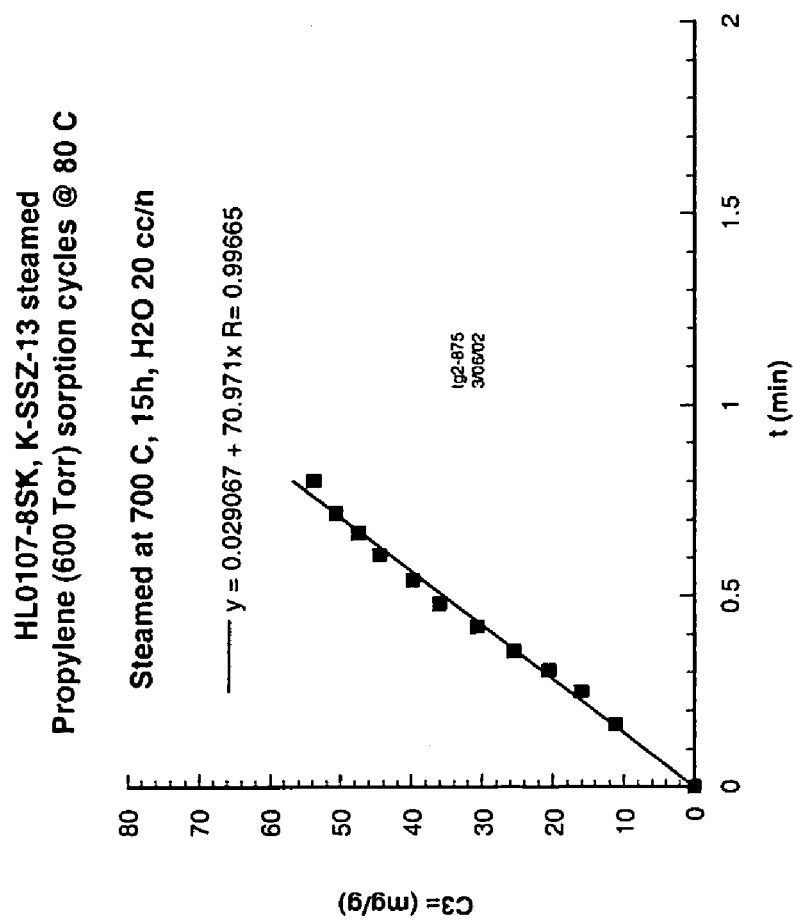
FIG. 6 shows the uptake rate of propylene on dealuminated K-SSZ-13 ($SiO_2/Al_2O_3$=160) at 353 K and 80 kPa.
Figure 7:
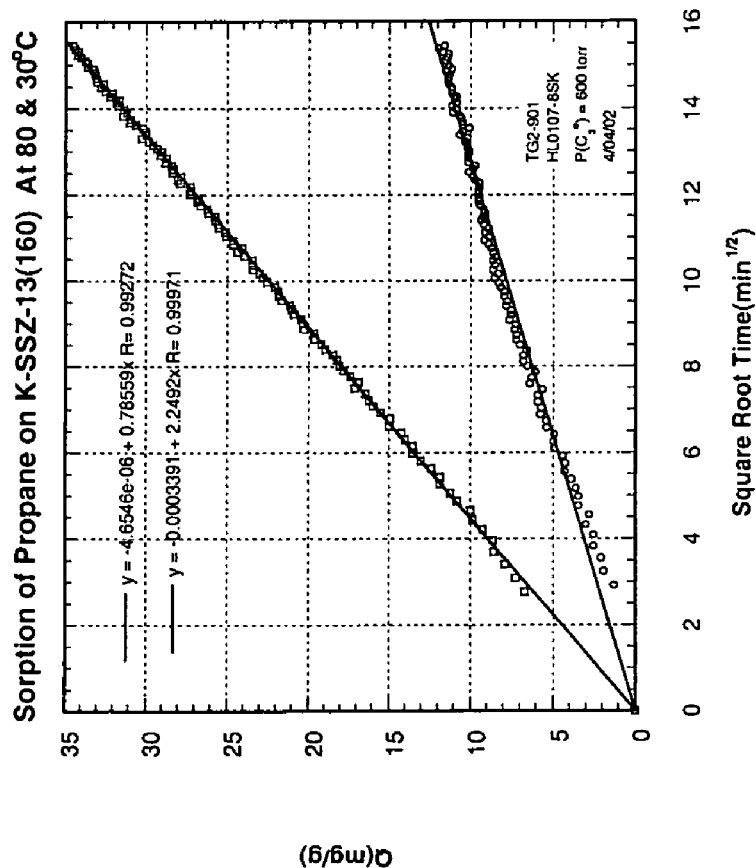
FIG. 7 shows the uptake rate of propane on dealuminated K-SSZ-13 ($SiO_2/Al_2O_3$=160) at 303 K and 353 K and 80 kPa.

The diffusion rate constants ($D/r^2$) for propylene and propane using the K-SSZ-13 ($SiO_2/Al_2O_3=160$) of Example 5 were measured using an adsorption uptake apparatus. The $D/r^2$ value for the adsorption of propylene at 353 K and 80 kPa is $1.8\times10^{-2}$ $sec^{-1}$ (see FIG. 6). The $D/r^2$ value of this material for the adsorption of propane at 353 K and 80 kPa is $1.6\times10^{-5}$ $sec^{-1}$ (see FIG. 7). The ratio of the propylene/propane diffusion rate constants is 1125.

Example 11 illustrates that the ratio of diffusivities of propylene and propane is very large ($R_D=D(C_3^=)/D(C_3^0)=1125$) as required for an effective kinetic-based separation scheme.

The invention having been thus described, it will be apparent that the same may be varied in many ways without departing from the spirit and scope of the invention, as defined by the following claims.

What is claimed is:

1. A process for kinetically separating a light hydrocarbon mixture comprising at least two components by preferentially adsorbing a first component on a zeolite adsorbent comprising 8-member rings of tetrahedra as the pore opening controlling hydrocarbon diffusion, wherein the zeolite adsorbent has been dealuminated and contains alkali metal cations balancing a framework charge, wherein a second component is not preferentially adsorbed, the process comprising the steps of:
   (a) contacting the light hydrocarbon mixture with the zeolite adsorbent having a $SiO_2/Al_2O_3$ molar ratio greater than about 80 and less than 180 and having a diffusion rate at least 50 times greater for the first component as compared to the second component; and
   (b) recovering at least one of the first component and the second component.

2. The process of claim 1 wherein the zeolite adsorbent is of a CHA structure.

3. The process of claim 2 wherein the zeolite adsorbent is SSZ-13.

4. The process of claim 1 wherein the dealuminating step comprises steaming the zeolite adsorbent.

5. The process of claim 4 wherein the steaming step is performed at a temperature between about 923 K and about 1123 K and a water pressure between about 5 kPa and about 202 kPa.

6. The process of claim 1 wherein the alkali metal cations are introduced by ion exchange at a pH greater than about 7.5.

7. The process of claim 1 wherein the cations are selected from the group consisting of sodium, potassium and cesium.

8. The process of claim 1 wherein the first component comprises propylene and the second component comprises propane.

* * * * *